(12) United States Patent
Jacques et al.

(10) Patent No.: US 11,510,861 B2
(45) Date of Patent: *Nov. 29, 2022

(54) HAIR TREATMENT PROCESS USING A COMPOSITION COMPRISING AT LEAST ONE CATIONIC ACRYLIC COPOLYMER

(71) Applicant: L'Oreal, Paris (FR)

(72) Inventors: Christophe Jacques, Herblay (FR); Nicolas Daubresse, La Celle Saint-Cloud (FR); Guillaume Ronchard, Saint-Chamond (FR)

(73) Assignee: L'OREAL, Paris (FR)

(*) Notice: Subject to any disclaimer, the term of this patent is extended or adjusted under 35 U.S.C. 154(b) by 1080 days.

This patent is subject to a terminal disclaimer.

(21) Appl. No.: 16/063,770

(22) PCT Filed: Dec. 22, 2016

(86) PCT No.: PCT/EP2016/082503
§ 371 (c)(1),
(2) Date: Jun. 19, 2018

(87) PCT Pub. No.: WO2017/109146
PCT Pub. Date: Jun. 29, 2017

(65) Prior Publication Data
US 2020/0268635 A1    Aug. 27, 2020

(30) Foreign Application Priority Data
Dec. 22, 2015    (FR) ........................................ 1563082

(51) Int. Cl.
*A61K 8/81*    (2006.01)
*A45D 7/06*    (2006.01)
*A61Q 5/06*    (2006.01)

(52) U.S. Cl.
CPC .............. *A61K 8/8158* (2013.01); *A45D 7/06* (2013.01); *A61K 8/8152* (2013.01); *A61Q 5/06* (2013.01)

(58) Field of Classification Search
CPC ................ A61K 8/8158; A61K 8/8152; A61K 2800/805; A45D 7/06; A61Q 5/06
See application file for complete search history.

(56) References Cited

U.S. PATENT DOCUMENTS 2,261,002 A    10/1941    Ritter
2,271,378 A    1/1942    Searle
(Continued)

FOREIGN PATENT DOCUMENTS

DE    19514630 A1    10/1996
EP    0080976 A1    6/1983
(Continued)

OTHER PUBLICATIONS

International Search Report for Application No. PCT/EP2016/082503, dated Feb. 1, 2017.
(Continued)

*Primary Examiner* — Vishal V Vasisth
(74) *Attorney, Agent, or Firm* — The Marbury Law Group, PLLC

(57) ABSTRACT

The present invention relates to a process for treating keratin fibres, especially the hair, comprising the following steps: —application to the keratin fibres of a composition comprising one or more cationic acrylic copolymers comprising at least the units obtained from the following monomers: a) monomer derived from acrylic or methacrylic esters or amides and comprising at least one cationic group, and b) alkyl acrylate or methacrylate monomer, and—application of heat to the keratin fibres using a heating tool, the application of heat possibly taking place before, during or
(Continued)

after the application of the composition, preferably during or after.

9 Claims, 1 Drawing Sheet

(56) References Cited

U.S. PATENT DOCUMENTS

| | | | |
|---|---|---|---|
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,589,978 A | 6/1971 | Kamal et al. | |
| 3,632,559 A | 1/1972 | Matter et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 4,001,432 A | 1/1977 | Green et al. | |
| 4,005,193 A | 1/1977 | Green et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,137,180 A | 1/1979 | Naik et al. | |
| 4,157,388 A | 6/1979 | Christiansen | |
| 4,165,367 A | 8/1979 | Chakrabarti | |
| 4,172,887 A | 10/1979 | Vanlerberghe et al. | |
| 4,185,087 A | 1/1980 | Morlino | |
| 4,197,865 A | 4/1980 | Jacquet et al. | |
| 4,217,914 A | 8/1980 | Jacquet et al. | |
| 4,240,450 A | 12/1980 | Grollier et al. | |
| 4,349,532 A | 9/1982 | Vanlerberghe et al. | |
| 4,591,610 A | 5/1986 | Grollier | |
| 4,702,906 A | 10/1987 | Jacquet et al. | |
| 4,719,282 A | 1/1988 | Nadolsky et al. | |
| 4,761,273 A | 8/1988 | Grollier et al. | |
| 4,839,166 A | 6/1989 | Grollier et al. | |
| 4,874,554 A | 10/1989 | Lange et al. | |
| 4,996,059 A | 2/1991 | Grollier et al. | |
| 5,089,252 A | 2/1992 | Grollier et al. | |
| 2016/0220471 A1 | 8/2016 | Baghdadli et al. | |

FOREIGN PATENT DOCUMENTS

| | | | | |
|---|---|---|---|---|
| EP | 0122324 A1 | 10/1984 | | |
| EP | 0337354 A1 | 10/1989 | | |
| EP | 0530974 A1 | 3/1993 | | |
| EP | 2883533 A1 * | 6/2015 | ............... | A61Q 5/12 |
| EP | 2883533 A1 | 6/2015 | | |
| FR | 1492597 A | 8/1967 | | |
| FR | 1583363 A | 10/1969 | | |
| FR | 2077143 A5 | 10/1971 | | |
| FR | 2080759 A1 | 11/1971 | | |
| FR | 2162025 A | 7/1973 | | |
| FR | 2190406 A2 | 2/1974 | | |
| FR | 2252840 A1 | 6/1975 | | |
| FR | 2270846 A1 | 12/1975 | | |
| FR | 2280361 A2 | 2/1976 | | |
| FR | 2316271 A1 | 1/1977 | | |
| FR | 2320330 A1 | 3/1977 | | |
| FR | 2336434 A1 | 7/1977 | | |
| FR | 2368508 A2 | 5/1978 | | |
| FR | 2383660 A1 | 10/1978 | | |
| FR | 2393573 A1 | 1/1979 | | |
| FR | 2413907 A1 | 8/1979 | | |
| FR | 2470596 A1 | 6/1981 | | |
| FR | 2505348 A1 | 11/1982 | | |
| FR | 2519863 A1 | 7/1983 | | |
| FR | 2542997 A1 | 9/1984 | | |
| FR | 2598611 A1 | 11/1987 | | |
| FR | 3008887 A1 | 1/2015 | | |
| FR | 3010311 A1 | 3/2015 | | |
| GB | 1546809 A | 5/1979 | | |
| JP | H07-309726 A | 11/1995 | | |
| JP | 5745266 B2 | 7/2015 | | |
| WO | 03/011969 A1 | 2/2003 | | |
| WO | 2017/109147 A1 | 6/2017 | | |

OTHER PUBLICATIONS

GOO Chemical: "Personal Care Product Catalogue for Cosmetics," Internet Citation, Jan. 2015, pp. 1-12, XP002759716, Retrieved from the Internet: http://www.goo-chem.co.jp/english/product/pdf/cosmetic/cosmetics_catalogue_en_2013.pdf [retrieved on Jul. 11, 2016].

Porter, M.R., "Handbook of Surfactants," published by Blackie & Son (Glasgow and London), 1991, pp. 116-178.

Todd, Charles, et al., "Volatile Silicone Fluids for Cosmetic Formulations," Cosmetics and Toiletries, vol. 91, Jan. 1976, pp. 29-32.

International Search Report for Application No. PCT/EP2016/082504, dated Feb. 15, 2017.

Anonymous: "Silsoft * A +, conditioning agent," Dec. 1, 2009, XP055294140, Retrieved from the Internet: http://s3.amazonaws.com/zanran_storage/www.momentive.com/ContentPages/45675670.pdf [retrieved on Aug. 8, 2016].

Floyd et al., "Performance-Driven: New Silicone CoPolymers—Experimenting with Dimethicone Copolyols for personal-care products," GCI, Global Cosmetic Industry, vol. 167, No. 3, Sep. 1, 2000, p. 26.

Ruetsch et al. "The Role of Cationic Conditioning Compounds in Reinforcement of the Cuticula," Journal of Cosmetic Science, XP055294540, Jan. 1, 2003, pp. 63-83. Retrieved from the Internet: http://journal.scconline.org/pdf/cc2003/cc054n01/p00063-p00083.pdf.

Non-Final Office Action for copending U.S. Appl. No. 16/063,799, dated Feb. 12, 2021.

Final Office Action for copending U.S. Appl. No. 16/063,799, dated Oct. 14, 2021.

* cited by examiner

HAIR TREATMENT PROCESS USING A COMPOSITION COMPRISING AT LEAST ONE CATIONIC ACRYLIC COPOLYMER

CROSS REFERENCE TO RELATED APPLICATIONS

This is a national stage application of PCT/EP2016/082503, filed internationally on Dec. 22, 2016, which claims priority to French Application No. 1563082, filed on Dec. 22, 2015, both of which are incorporated by reference herein in their entireties.

The present invention relates to a hair treatment process using a composition comprising at least one particular cationic acrylic copolymer.

Many non-invasive technologies now exist for satisfying styling needs. Styling products are usually used to construct and structure the hairstyle and to give it long-lasting hold. These compositions generally comprise one or more fixing film-forming polymers, in a cosmetically acceptable medium. These polymers allow the formation of a coating film on the hair, or the formation of micro-welds between the individual hairs, thus ensuring the hairstyle hold.

Styling products are generally in the form of lacquers, mousses or gels. In particular, styling gels are often used in order to obtain strong fixing of the hairstyle. Styling gels are solutions of one or more fixing film-forming polymers, thickened or gelled with one or more thickening polymers.

However, the effects provided by these technologies disappear during the first shampoo wash and it is necessary to reapply them in order to obtain the desired effect. This imposes a more or less long and tedious routine on the consumer. For example, for a blow-drying product for frizzy hair, after applying the styling spray, the product needs to be distributed uniformly over the entire head of hair followed by performing blow-drying, which may take from 5 to 45 minutes depending on the desired result.

In contrast, long-lasting shape products allow the structure of the fibre to be definitively modified by breaking (reducing) the disulfide bonds which impose the original shape of the hair, followed by re-bridging (e.g.: oxidation of the cysteines to cystine after a mechanical action such as the insertion of curlers in the case of permanent waving). These products must, however, be reapplied at the root once hair regrowth occurs in order to conserve a uniform result. The results are irreversible and damage the hair. The superposition of relaxing products, for example, may cause discomfort and, in the long-term, lead to real degradation of the fibre which may be up to the point of breakage.

The object of a semi-permanent styling product is to offer satisfaction as regards the durability of the styling effects after one or more shampoo washes, while at the same time preserving the integrity of the fibre so as to offer the consumer timesaving and improved safety. The term "styling effect" means performance in terms of manageability, provision of body, curl definition, volume control, sheen, ease of shaping by natural drying, blow-drying and/or using flat tongs, and hairsetting. Ideally, it is also expected of this type of product that it be readily removable by means of an action or by a composition acting as a makeup remover.

Furthermore, the product must not generate static electricity.

There is thus a need to formulate a treatment, especially a treatment which gives the treated fibre coating of the fibre, which satisfies the following criteria:

being adherent to the fibre and remaining perceptible after several shampoo washes, allowing the hair to be easily and durably shaped, affording good cosmetic qualities, being simple to use, without any risk of damaging the hair, being compatible with the hair treatments conventionally used (shampooing, hair conditioning, colouring), but also with sebum.

It has now been discovered that the use of a composition containing at least one particular cationic acrylic polymer, which is preferably water-insoluble, combined with the use of a heating tool, for example a hair dryer or a straightening iron, makes it possible to generate coating around the hair fibre, which is persistent with respect to shampooing, and which provides the desired styling properties, while at the same time being friendly to the fibre. What is more, this coating is persistent with respect to shampooing. Furthermore, this composition applied according to this process has good working qualities (distribution, disentangling of dry and wet hair, individualization).

A subject of the invention is thus especially a process for treating keratin fibres, especially the hair, comprising the following steps:

application to the keratin fibres of a composition comprising one or more cationic acrylic copolymers comprising at least the units obtained from the following monomers:

a) monomer derived from acrylic or methacrylic esters or amides and comprising at least one cationic group, and b) alkyl acrylate or methacrylate monomer, and application of heat to the keratin fibres using a heating tool, the application of heat possibly taking place before, during or after the application of the composition, preferably during or after.

It was observed that the fibres thus treated have a coating that is persistent with respect to shampooing. The composition applied according to this process gives shaping properties and has good working qualities (distribution, disentangling of dry and wet hair, individualization) on application and after shampooing.

Other characteristics, aspects, objects and advantages of the present invention will emerge even more clearly on reading the description, the examples that follow, and on reading the figures.

Figure 1A:
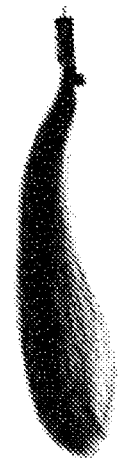
FIGS. 1A and 2A are photographs of locks of hair on which different compositions have been applied through a protocol implemented five times.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

According to the present application, "keratin fibres" means human keratin fibres and more specifically hair.

Application Step

The process according to the invention comprises a step of applying a composition to keratin fibres.

Copolymer

The composition that is useful according to the process according to the invention comprises at least one acrylic cationic copolymer, comprising at least the units obtained from the following monomers:

a) monomer derived from acrylic or methacrylic esters or amides and comprising at least one cationic group, and b) alkyl acrylate or methacrylate monomer, the alkyl radical comprising from 1 to 30 carbon atoms, preferably 1 to 22 carbon atoms, better still 1 to 10 carbon atoms and preferentially 2 to 6 carbon atoms.

For the purposes of the present invention, the term "cationic compound or group" means a compound or group bearing a permanent cationic charge or a charge obtained by protonation of a function (cationizable), such as an amine function, by the protons of the medium.

Preferably, the copolymer according to the invention is water-insoluble. For the purposes of the present invention, the term "water-insoluble" refers to a compound that is insoluble in water at ordinary temperature (25° C.) and at atmospheric pressure (760 mmHg or $1.013 \times 10^5$ Pa) (solubility of less than 5%, preferably 1% and even more preferentially 0.1%).

Preferentially, the acrylic cationic copolymer contains c) at least a third unit obtained from a polymerizable ethylenic monomer, preferably from a monomer having the following formula:

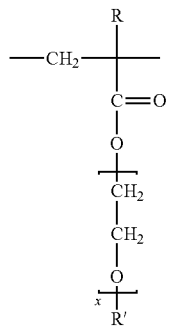

(A')

in which R and R', which may be identical or different, represent a hydrogen atom, a C1-C10 and preferably C1-C4 alkyl radical; preferably, R is a methyl radical; better still, R is a methyl radical and R' is an ethyl radical;

x ranging from 1 to 10, preferably from 1 to 3, and better still x is 1.

More particularly, the acrylic cationic copolymer present in the composition according to the invention comprises at least units obtained from the following two lists of monomers:

a) monomer derived from acrylic or methacrylic esters or amides and comprising at least one cationic group, having the following formulae:

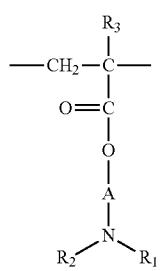

(I)

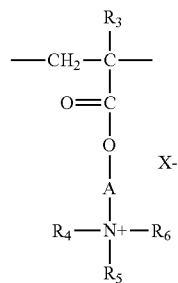

(II)

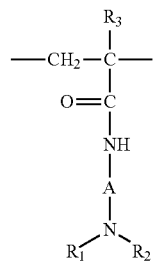

(III)

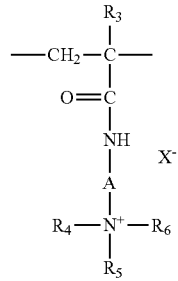

(IV)

in which:

$R_3$, which may be identical or different, denote a hydrogen atom or a $CH_3$ group;

A, which may be identical or different, represent a linear or branched divalent alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl group, and preferably an alkyl group containing from 1 to 6 carbon atoms;

$R_1$ and $R_2$, which may be identical or different, represent a hydrogen atom or an alkyl group containing from 1 to 6 carbon atoms, and preferably methyl or ethyl;

$X^-$ denotes an anion derived from a mineral or organic acid, such as a methosulfate anion or a halide such as chloride or bromide, b) $C_1$-$C_{30}$, preferably $C_1$-$C_{22}$, preferentially $C_1$-$C_{10}$ and better still $C_2$-$C_6$ alkyl acrylate or methacrylate monomer.

Even more preferentially, the acrylic cationic copolymer present in the composition according to the invention comprises at least the units obtained from the following monomers:

a) monomer derived from acrylic or methacrylic esters or amides and comprising at least one cationic group, having the following formulae:

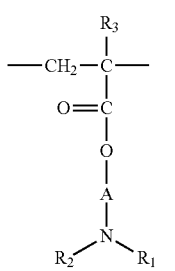
(I)

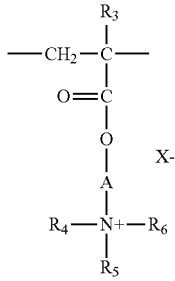
(II)

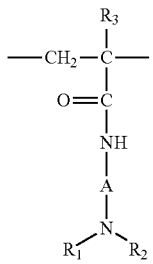
(III)

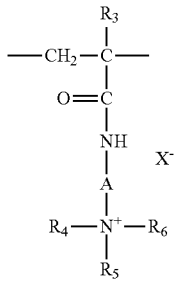
(IV)

in which:
- $R_3$, which may be identical or different, denote a hydrogen atom or a $CH_3$ group;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- $R_4$, $R_5$ and $R_6$, which may be identical or different, represent an alkyl group containing from 1 to 18 carbon atoms or a benzyl group, and preferably an alkyl group containing from 1 to 6 carbon atoms;
- $R_1$ and $R_2$, which may be identical or different, represent a hydrogen atom or an alkyl group containing from 1 to 6 carbon atoms, and preferably methyl or ethyl;
- $X^-$ denotes an anion derived from a mineral or organic acid, such as a methosulfate anion or a halide such as chloride or bromide, preferably, formulae (I) and (II)

b) $C_1$-$C_{30}$, preferably $C_1$-$C_{22}$, preferentially $C_1$-$C_{10}$ and better still $C_2$-$C_6$ alkyl acrylate or methacrylate monomer; and c) polymerizable ethylenic monomer, preferably from a monomer having the following formula

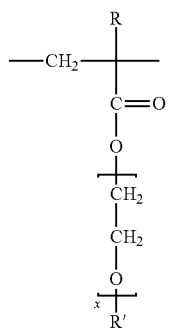
(A')

in which R and R', which may be identical or different, represent a hydrogen atom, a $C_1$-$C_{10}$ and preferably $C_1$-$C_4$ alkyl radical; preferably, R is a methyl radical; better still, R is a methyl radical and R' is an ethyl radical;

x ranging from 1 to 10, preferably from 1 to 3, and better still x is 1.

Even more particularly, the composition that is useful in the process according to the invention comprises at least one copolymer comprising at least the units obtained from the following monomers:

a) a monomer derived from acrylic or methacrylic esters of formula (I) or (II) as described previously, preferably from formula (II), b) a $C_1$-$C_{22}$, preferably $C_1$-$C_{10}$ and better still $C_2$-$C_6$ alkyl acrylate or methacrylate monomer, c) a monomer of formula (A') as described previously.

Most particularly, the composition comprises one or more cationic acrylic copolymers, which are preferably water-insoluble, bearing the following units:

a) methacryloyloxyethyltrimethylammonium salt, b) butyl methacrylate, and c) ethoxyethyl methacrylate.

Such copolymers are described, for example, in JP5745266. Preferably, the polymer contains the preceding three monomers in the following proportions relative to the total number of monomer units, by weight in the constituted copolymer, without taking into account the salts thereof:

a) in a proportion of 0.5% to 20%, preferably between 1% and 5%;

a) in a proportion of 20% to 98%, preferably between 40% and 97%; and a) in a proportion of 1.5% to 95%, preferably between 2% and 55%.

Preferably, the copolymer is not amphoteric, i.e. it does not comprise any units bearing an anionic charge.

Preferably, the units of the copolymer are all methacrylate derivatives.

Even more particularly, the copolymer corresponds to the copolymer whose INCI name is Polyquaternium-99, for instance the polymer sold by the company GOO-Chemical under the name Plascize L-514.

It is the butyl methacrylate/ethoxyethyl methacrylate/methacryloyloxyethyltrimethylammonium chloride copolymer, at 30% in ethanol:

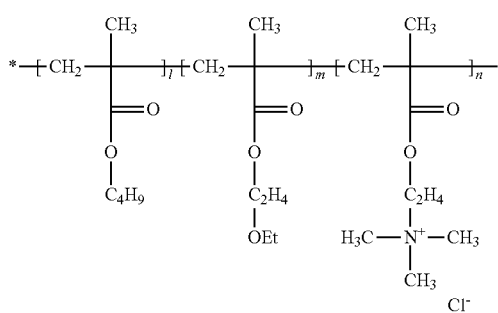

The content of copolymer in the composition that is useful in the process according to the invention may range from 0.05% to 15% by weight relative to the total weight of the composition, preferably from 0.1% to 10% by weight and more preferentially from 1% to 7% by weight relative to the total weight of the composition.

Solvents

The composition comprises a cosmetically acceptable medium which generally comprises water, non-aqueous solvents, silicone solvents, and a mixture thereof.

More particularly, the organic solvents are chosen from linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, especially of $C_1$-$C_4$, for instance diethylene glycol monoethyl ether or monobutyl ether, alone or as a mixture.

More particularly, the silicone solvents are chosen from volatile and non-volatile silicones.

When they are volatile, the silicones are more particularly chosen from those with a boiling point of between 60° C. and 260° C., and even more particularly from:

(i) cyclic polydialkylsiloxanes containing from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxanes/methylalkylsiloxane type, such as Volatile Silicone® FZ 3109 sold by the company Union Carbide, of formula:

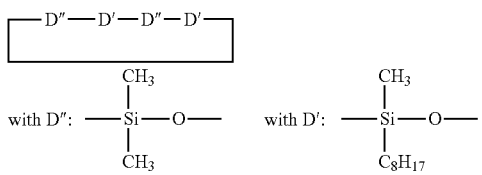

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, "Volatile Silicone Fluids for Cosmetics".

Preferably, alcohols are preferred, and, more particularly ethanol is preferred.

When they are present, the usual organic solvents described above usually represent from 1% to 95% by weight, more preferentially from 2% to 60% by weight, preferably from 3% to 55% by weight and better still from 8% to 50% by weight, relative to the total weight of the composition.

Preferably, the composition that is useful in the process according to the invention is non-colouring.

For the purposes of the present invention, the term "non-colouring composition" means a composition which does not comprise any direct dye or oxidation dye precursor (oxidation base and coupler) or any compound which, by reaction, gives a coloured species in the composition or on the fibres, usually used for colouring human keratin fibres, or alternatively, if it does comprise any, the total amount does not exceed 0.005% by weight relative to the weight of the composition. Specifically, at such a content, only the composition would be dyed, i.e. no colouring effect would be observed on the keratin fibres.

It is recalled that oxidation dye precursors, oxidation bases and couplers are colourless or sparingly coloured compounds, which, via a condensation reaction in the presence of an oxidizing agent, give a coloured species. With regard to direct dyes, these compounds are coloured and have a certain affinity for keratin fibres.

The composition that is useful in the process according to the invention may comprise one or more additives chosen from a thickening polymer, a surfactant, a conditioning agent such as functionalized silicones, and a fatty substance, and a mixture thereof.

Thickeners

The composition may especially comprise one or more mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas may be obtained by high-temperature hydrolysis of a volatile silicon compound in an oxyhydrogen flame, producing a finely divided silica. This process makes it possible in particular to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:
trimethylsiloxyl groups, which are obtained in particular by treating fumed silica in the presence of hexamethyldisilazane. Silicas thus treated are known as Silica silylate according to the CTFA (6th Edition, 1995). They are sold, for example, under the references Aerosil R812® by Degussa and Cab-O-Sil TS-530® by Cabot.
dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the mineral thickener may represent from 0.1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropanesulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum) and crosslinked acrylic acid or acrylamidopropanesulfonic acid homopolymers, and preferably from cellulose-based thickeners in particular with hydroxyethylcellulose.

The content of organic thickener(s), if they are present, usually ranges from 0.01% to 20% by weight and preferably from 0.1% to 5% by weight relative to the weight of the composition.

Surfactants

According to a particular embodiment of the invention, the composition also comprises one or more surfactants.

In particular, the surfactant(s) are chosen from cationic, anionic, amphoteric, zwitterionic and nonionic surfactants, and preferentially cationic surfactants.

The cationic surfactant(s) that may be used in the composition according to the process of the invention comprise, for example, optionally polyoxyalkylenated primary, secondary or tertiary fatty amine salts, quaternary ammonium salts, and mixtures thereof.

Examples of quaternary ammonium salts that may in particular be mentioned include:
those corresponding to the general formula (A4) below:

in which formula (A4):
$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and
$X^-$ represents an organic or mineral anionic counterion, such as that chosen from halides, acetates, phosphates, nitrates, $(C_1$-$C_4)$alkyl sulfates, $(C_1$-$C_4)$alkyl- or $(C_1$-$C_4)$ alkylaryl sulfonates, in particular methyl sulfate and ethyl sulfate.

The aliphatic groups of $R_8$ to $R_{11}$ may also comprise heteroatoms in particular such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, $(C_{12}$-$C_{22})$alkylamido($C_2$-$C_6$)alkyl, $(C_{12}$-$C_{22})$alkyl acetate, and $C_1$-$C_{30}$ hydroxyalkyl groups; $X^-$ is an anionic counterion chosen from halides, phosphates, acetates, lactates, $(C_1$-$C_4)$alkyl sulfates, and $(C_1$-$C_4)$alkylsulfonates or $(C_1$-$C_4)$alkylarylsulfonates.

Among the quaternary ammonium salts of formula (A4), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;
quaternary ammonium salts of imidazoline, for instance those of formula (A5) below:

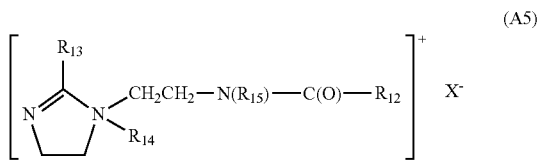

(A5)

in which formula (A5):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or mineral anionic counterion, such as that chosen from halides, phosphates, acetates, lactates, ($C_1$-$C_4$)alkyl sulfates, ($C_1$-$C_4$)alkyl or ($C_1$-$C_4$) alkylaryl sulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, particularly of formula (A6) below:

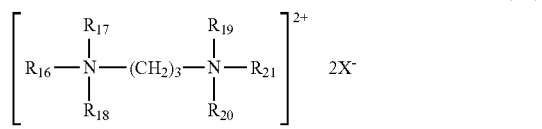

(A6)

in which formula (A6):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group —$(CH_2)_3$—$N^+$ $(R_{16a})(R_{17a})(R_{18a})$, $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represents an organic or mineral anionic counterion, such as that chosen from halides, acetates, phosphates, nitrates, alkyl($C_1$-$C_4$) sulfates, alkyl($C_1$-$C_4$)- or alkyl($C_1$-$C_4$) aryl-sulfonates, more particularly methyl sulfate and ethyl sulfate.

Such compounds are, for example, Finquat CT-P, sold by the company Finetex (Quatemium 89), and Finquat CT, sold by the company Finetex (Quatemium 75);

quaternary ammonium salts containing one or more ester functions, such as those of formula (A7 below:

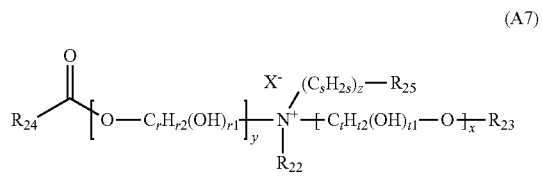

(A7)

in which formula (A7):

$R_{22}$ is chosen from $C_1$-$C_6$ alkyl groups and $C_1$-$C_6$ hydroxyalkyl or $C_1$-$C_6$ dihydroxyalkyl groups;

$R_{23}$ is chosen from:
the group $R_{26}$—$\overset{O}{\underset{\|}{C}}$—, saturated or unsaturated, linear or branched $C_1$-$C_{22}$ hydrocarbon-based groups $R_{27}$,
a hydrogen atom, $R_{25}$ is chosen from:
the group $R_{28}$—$\overset{O}{\underset{\|}{C}}$—, saturated or unsaturated, linear or branched $C_1$-$C_6$ hydrocarbon-based groups $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10;

$X^-$ represents an organic or mineral anionic counterion,
with the proviso that the sum x+y+z is from 1 to 15, that when x is 0 then $R_{23}$ denotes $R_{27}$, and that when z is 0 then $R_{25}$ denotes a linear or branched, saturated or unsaturated $C_1$-$C_6$ hydrocarbon-based radical $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, have the value 0 or 1.

Advantageously, y is equal to 1.

Preferably, r, s and t, which may be identical or different, have the value 2 or 3 and more particularly still are equal to 2.

The anionic counterion $X^-$ is preferably a halide, such as chloride, bromide or iodide; a $(C_1\text{-}C_4)$alkyl sulfate or a $(C_1\text{-}C_4)$alkyl- or $(C_1\text{-}C_4)$alkylarylsulfonate. However, use may be made of methanesulfonate, phosphate, nitrate, tosylate, an anion derived from an organic acid, such as acetate or lactate, or any other anion which is compatible with the ammonium having an ester function.

The anionic counterion $X^-$ is even more particularly chloride, methyl sulfate or ethyl sulfate.

Use is made more particularly, in the composition that is that is useful in the process according to the invention, of the ammonium salts of formula (A7) in which:

$R_{22}$ denotes a methyl or ethyl group, x and y are equal to 1, z is equal to 0 or 1, r, s and t are equal to 2, $R_{23}$ is chosen from:

the group

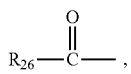

methyl, ethyl or $C_{14}\text{-}C_{22}$ hydrocarbon-based groups, a hydrogen atom, $R_{25}$ is chosen from:

the group

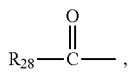

a hydrogen atom, $R_{24}$, $R_{26}$ and $R_{28}$, which may be identical or different, are chosen from linear or branched, saturated or unsaturated $C_{13}\text{-}C_{17}$ hydrocarbon-based groups, and preferably from linear or branched, saturated or unsaturated $C_{13}\text{-}C_{17}$ alkyl and alkenyl groups.

Advantageously, the hydrocarbon-based radicals are linear.

Among the compounds of formula (A7), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition that is that is useful in the process according to the invention may contain, for example, a mixture of quaternary ammonium monoester, diester and triester salts with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts comprising at least one ester function comprise two ester functions.

Among the cationic surfactants that may be present in the composition, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

The term "anionic surfactant" means a surfactant comprising, as ionic or ionizable groups, only anionic groups. These anionic groups are preferably chosen from the groups $-C(O)OH$, $-C(O)O^-$, $-SO_3H$, $-S(O)_2O$, $-OS(O)_2OH$, $-OS(O)_2O-$, $-P(O)OH_2$, $-P(O)_2O^-$, $-P(O)O_2^-$, $-P(OH)_2$, $=P(O)OH$, $-P(OH)O^-$, $=P(O)O^-$ and $=POH$, $=PO^-$, the anionic parts comprising a cationic counterion such as those derived from an alkali metal, an alkaline-earth metal, an amine or an ammonium.

As examples of anionic surfactants that may be used in the composition, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6\text{-}C_{24}$ alkyl monoesters of polyglycosidepolycarboxylic acids may be chosen from $C_6\text{-}C_{24}$ alkyl polyglycoside-citrates, $C_6\text{-}C_{24}$ alkyl polyglycoside-tartrates and $C_6\text{-}C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine and triisopropanolamine salts, and 2-amino-2- methyl-1-propanol, 2-amino-2-methyl-1,3-propanediol and tris(hydroxymethyl)aminomethane salts.

Use is preferably made of alkali metal or alkaline-earth metal salts and in particular of sodium or magnesium salts.

Among the anionic surfactants mentioned, use is preferably made of $(C_6-C_{24})$alkyl sulfates, $(C_6-C_{24})$alkyl ether sulfates comprising from 2 to 50 ethylene oxide units, in particular in the form of alkali metal, ammonium, amino alcohol and alkaline-earth metal salts, or a mixture of these compounds.

In particular, it is preferred to use $(C_{12}-C_{20})$alkyl sulfates, $(C_{12}-C_{20})$alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The amphoteric or zwitterionic surfactant(s), which are preferably non-silicone, which may be used in the present invention may in particular be derivatives of optionally quatemized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of $(C_8-C_{20})$alkyl betaines, sulfobetaines, $(C_8-C_{20})$alkylamido$(C_3-C_8)$alkyl betaines and $(C_8-C_{20})$alkylamido$(C_6-C_8)$alkyl sulfobetaines.

Among the optionally quaternized secondary or tertiary aliphatic amine derivatives that may be used, as defined above, mention may also be made of the compounds of respective structures (A1) and (A2) below:

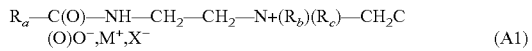

in which formula (A1):
$R_a$ represents a $C_{10}-C_{30}$ alkyl or alkenyl group derived from an acid $R_a$—COOH preferably present in hydrolysed copra oil, or a heptyl, nonyl or undecyl group;
$R_b$ represents a β-hydroxyethyl group; and
$R_c$ represents a carboxymethyl group;
$M^+$ represents a cationic counterion derived from an alkali metal or alkaline-earth metal, such as sodium, an ammonium ion or an ion derived from an organic amine, and
$X^-$ represents an organic or mineral anionic counterion, such as that chosen from halides, acetates, phosphates, nitrates, $(C_1-C_4)$alkyl sulfates, $(C_1-C_4)$alkyl- or $(C_1-C_4)$alkylaryl sulfonates, in particular methyl sulfate and ethyl sulfate; or alternatively $M^+$ and $X^-$ are absent;

$$R_{a'}-C(O)-NH-CH_2-CH_2-N(B)(B') \quad (A2)$$

in which formula (A2):
B represents the group —$CH_2$—$CH_2$—O—X';
B' represents the group —$(CH_2)_z$Y', with z=1 or 2;
X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
$R_{a'}$ represents a $C_{10}-C_{30}$ alkyl or alkenyl group of an acid $R_{a'}$—C(O)OH preferably present in coconut oil or in hydrolysed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of the compounds of formula (A3):

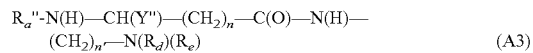

in which formula (A3):
Y" represents the group —C(O)OH, —C(O)OZ", —$CH_2$—CH(OH)—$SO_3$H or the group —$CH_2$—CH(OH)—$SO_3$—Z";
$R_d$ and $R_e$, independently of each other, represent a $C_1-C_4$ alkyl or hydroxyalkyl;
Z" represents a cationic counterion derived from an alkali metal or alkaline-earth metal, such as sodium, an ammonium ion or an ion derived from an organic amine;
$R_a$" represents a $C_{10}-C_{30}$ alkyl or alkenyl group derived from an acid $R_a$"'—C(O)OH preferably present in coconut oil or in hydrolysed linseed oil.
n and n' denote, independently of each other, an integer ranging from 1 to 3.

Among the compounds of formula (A3), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of $(C_8-C_{20})$alkylbetaines such as cocoylbetaine, and $(C_8-C_{20})$alkylamido$(C_3-C_5)$alkylbetaines such as cocamidopropylbetaine, and mixtures thereof. More preferentially, the amphoteric or zwitterionic surfactant(s) are chosen from cocamidopropylbetaine and cocoylbetaine.

Examples of nonionic surfactants that may be used in the composition used according to the invention are described, for example, in the '*Handbook of Surfactants*' by M. R. Porter, published by Blackie & Son (Glasgow and London), 1991, pp. 116-178.

Mention may be made, as examples of oxyalkylenated nonionic surfactants, of:
oxyalkylenated $(C_8-C_{24})$alkylphenols;
saturated or unsaturated, linear or branched, oxyalkylenated $C_8-C_{30}$ alcohols;
saturated or unsaturated, linear or branched, oxyalkylenated $C_8-C_{30}$ amides;
esters of saturated or unsaturated, linear or branched, $C_8-C_{30}$ acids and of polyethylene glycols;
polyoxyethylenated esters of saturated or unsaturated, linear or branched, $C_8-C_{30}$ acids and of sorbitol;
esters of fatty acids and of sucrose;
$(C_8-C_{30})$alkylpolyglycosides, $(C_8-C_{30})$alkenylpolyglycosides, which are optionally oxyalkylenated (0 to 10 oxyalkylene units) and which comprise 1 to 15 glucose units, $(C_8-C_{30})$alkylglucoside esters;
saturated or unsaturated oxyethylenated plant oils;

condensates of ethylene oxide and/or of propylene oxide, inter alia, alone or as mixtures;

N—($C_8$-$C_{30}$)alkylglucamine derivatives and N—($C_8$-$C_{30}$)acyl-methylglucamine derivatives;

aldobionamides;

amine oxides;

oxyethylenated and/or oxypropylenated silicones;

the surfactants containing a number of moles of ethylene oxide and/or of propylene oxide ranging advantageously from 1 to 100, more particularly from 2 to 100, preferably from 2 to 50 and more advantageously from 2 to 30. Advantageously, the nonionic surfactants do not comprise any oxypropylene units.

In accordance with a preferred embodiment of the invention, the oxyalkylenated nonionic surfactants are chosen from oxyethylenated $C_8$-$C_{30}$ alcohols comprising from 1 to 100 mol and more particularly from 2 to 100 mol of ethylene oxide; polyoxyethylenated esters of saturated or unsaturated, linear or branched $C_8$-$C_{30}$ acids and of sorbitan comprising from 1 to 100 mol and better still from 2 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to formula (A8) below:

$$R_{29}O—[CH_2—CH(CH_2OH)—O]_m—H \qquad (A8)$$

in which formula (A8):

$R_{29}$ represents a linear or branched $C_8$-$C_{40}$ and preferably $C_8$-$C_{30}$ alkyl or alkenyl radical; and m represents a number ranging from 1 to 30 and preferably from 1 to 10.

As examples of compounds of formula (A8) that are suitable within the context of the invention, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

The alcohol of formula (A8) may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The surfactants may be present in an amount ranging from 0.01% to 15% by weight, preferably from 0.05% to 10% by weight and better still from 0.1% to 5% by weight, relative to the total weight of the composition.

Functionalized Silicones

The composition may comprise an organomodified polysiloxane comprising at least one functional group preferably chosen from amine groups, alkoxy groups, hydroxyl groups and reactive groups.

Organopolysiloxanes are defined in greater detail in Walter Noll's *Chemistry and Technology of Silicones* (1968), Academic Press.

The organomodified silicones that may be used in accordance with the invention are silicones comprising in their structure one or more organofunctional groups as mentioned previously, attached via a hydrocarbon-based group.

The organomodified silicone(s) may be chosen from one or more amino silicones. The term "amino silicone" denotes any silicone comprising at least one primary, secondary or tertiary amine or a quaternary ammonium group.

The weight-average molecular masses of these amino silicones may be measured by gel permeation chromatography (GPC) at room temperature (25° C.), as polystyrene equivalents. The columns used are µ styragel columns. The eluent is THF and the flow rate is 1 ml/min. 200 µl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

$$HO-\left[\begin{array}{c} CH_3 \\ | \\ Si-O \\ | \\ CH_3 \end{array}\right]_{x'} \left[\begin{array}{c} OH \\ | \\ Si-O \\ | \\ (CH_2)_3 \\ | \\ NH \\ | \\ (CH_2)_2 \\ | \\ NH_2 \end{array}\right]_{y'} -H \qquad (A)$$

in which x' and y' are integers such that the weight-average molecular weight (Mw) is between 5000 and 500 000 approximately;

b) the amino silicones corresponding to formula (B):

$$R'_a G_{3-a}\text{-Si}(OSiG_2)_n\text{-}(OSiG_b R'_{2-b})_m—O—SiG_{3-a}\text{-}R'_a \qquad (B)$$

in which:

G, which may be identical or different, denotes a hydrogen atom or a phenyl, OH or $C_1$-$C_8$ alkyl group, for example methyl, or a $C_1$-$C_8$ alkoxy, for example methoxy, a, which may be identical or different, denotes 0 or an integer from 1 to 3, in particular 0, b denotes 0 or 1, in particular 1, m and n are numbers such that the sum (n+m) ranges from 1 to 2000 and in particular from 50 to 150, n possibly denoting a number from 0 to 1999 and especially from 49 to 149, and m possibly denoting a number from 1 to 2000 and especially from 1 to 10;

R', which may be identical or different, denotes a monovalent radical of formula —CqH2qL in which q is a number ranging from 2 to 8 and L is an optionally quatemized amino group chosen from the following groups: —N(R")$_2$; —N+(R")$_3$A-; —NR"-Q-N(R")$_2$ and —NR"-Q-N+(R")$_3$A-, in which R", which may be identical or different, denotes hydrogen, phenyl, benzyl, or a saturated monovalent hydrocarbon-based radical, for example a $C_1$-$C_{20}$ alkyl radical; Q denotes a linear or branched $C_rH_{2r}$ group, r being an integer ranging from 2 to 6, preferably from 2 to 4; and A- represents a cosmetically acceptable anion, especially a halide such as fluoride, chloride, bromide or iodide.

Preferably, the amino silicones are chosen from the amino silicones of formula (B).

Preferably, the amino silicones of formula (B) are chosen from the amino silicones corresponding to formulae (C), (D), (E), (F) and/or (G) below.

According to a first embodiment, the amino silicones corresponding to formula (B) are chosen from the silicones known as "trimethylsilyl amodimethicone" corresponding to formula (C):

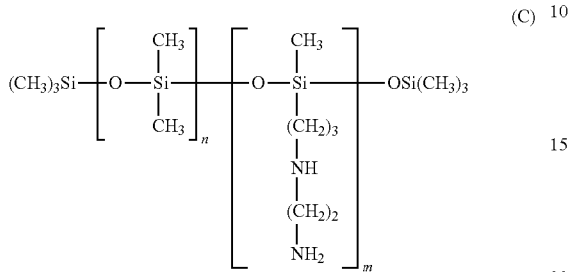

in which m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10.

According to a second embodiment, the amino silicones corresponding to formula (B) are chosen from the silicones of formula (D) below:

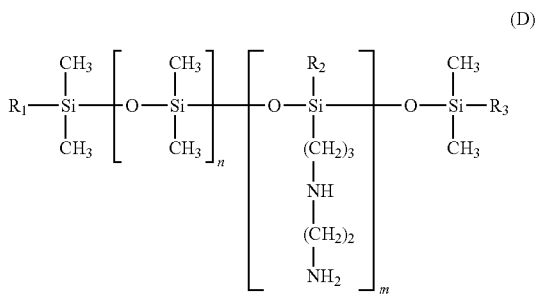

in which:
- m and n are numbers such that the sum (n+m) ranges from 1 to 1000 and in particular from 50 to 250 and more particularly from 100 to 200; it being possible for n to denote a number from 0 to 999 and in particular from 49 to 249 and more particularly from 125 to 175, and for m to denote a number from 1 to 1000 and in particular from 1 to 10, and more particularly from 1 to 5;
- R1, R2 and R3, which may be identical or different, represent a hydroxyl or C1-C4 alkoxy radical, at least one of the radicals R1 to R3 denoting an alkoxy radical.

Preferably, the alkoxy radical is a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular mass (Mw) of these silicone preferably ranges from 2000 to 1 000 000 and even more particularly from 3500 to 200 000.

According to a third embodiment, the amino silicones corresponding to formula (B) are chosen from the silicones of formula (E) below:

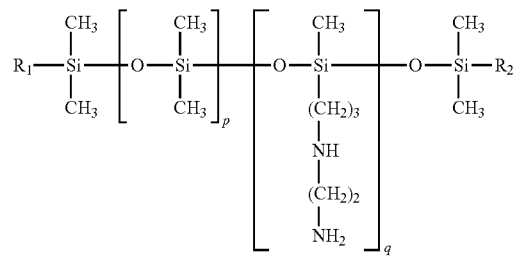

in which:
- p and q are numbers such that the sum (p+q) ranges from 1 to 1000, in particular from 50 to 350 and more particularly from 150 to 250; it being possible for p to denote a number from 0 to 999 and especially from 49 to 349 and more particularly from 159 to 239, and for q to denote a number from 1 to 1000, especially from 1 to 10 and more particularly from 1 to 5;
- R1 and R2, are different, represent a hydroxyl or C1-C4 alkoxy radical, at least one of the radicals R1 or R2 denoting an alkoxy radical.

Preferably, the alkoxy radical is a methoxy radical.

The hydroxy/alkoxy mole ratio generally ranges from 1:0.8 to 1:1.1, preferably from 1:0.9 to 1:1 and is more particularly equal to 1:0.95.

The weight-average molecular mass (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones whose structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The numerical mean size of the silicone particles in the emulsion generally ranges from 3 nm to 500 nm. Preferably, especially as amino silicones of formula (E), use is made of microemulsions whose mean particle size ranges from 5 nm to 60 nm (limits inclusive) and more particularly from 10 nm to 50 nm (limits inclusive). Thus, use may be made according to the invention of the amino silicone microemulsions of formula (E) sold under the names Finish CT 96 E® or SLM 28020® by the company Wacker.

According to a fourth embodiment, the amino silicones corresponding to formula (B) are chosen from the silicones of formula (F) below:

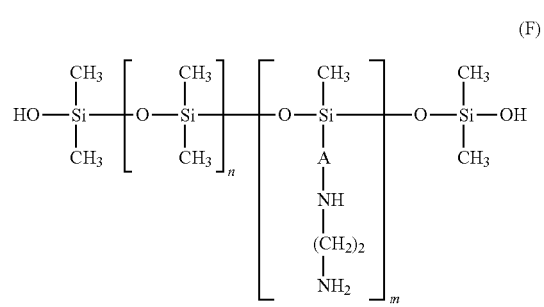

in which:
- m and n are numbers such that the sum (n+m) ranges from 1 to 2000 and in particular from 50 to 150, it being possible for n to denote a number from 0 to 1999 and especially from 49 to 149, and for m to denote a number from 1 to 2000 and especially from 1 to 10;
- A denotes a linear or branched alkylene radical containing from 4 to 8 carbon atoms and preferably 4 carbon atoms. This radical is preferably linear.

The weight-average molecular mass (Mw) of these amino silicones preferably ranges from 2000 to 1 000 000 and even more particularly from 3500 to 200 000.

A silicone corresponding to this formula is, for example, Xiameter MEM 8299 Emulsion from Dow Corning.

According to a fifth embodiment, the amino silicones corresponding to formula (B) are chosen from the silicones of formula (G) below:

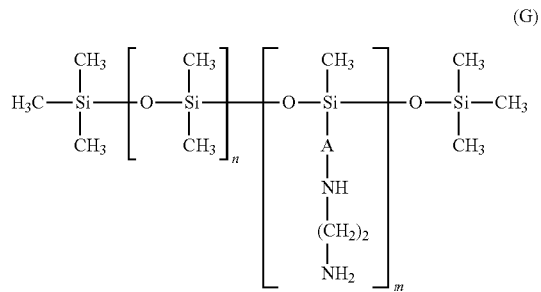
(G)

in which:
- m and n are numbers such that the sum (n+m) ranges from 1 to 2000 and in particular from 50 to 150, it being possible for n to denote a number from 0 to 1,999 and especially from 49 to 149, and for m to denote a number from 1 to 2000 and especially from 1 to 10;
- A denotes a linear or branched alkylene radical containing from 4 to 8 carbon atoms and preferably 4 carbon atoms. This radical is preferably branched.

The weight-average molecular mass (Mw) of these amino silicones preferably ranges from 500 to 1 000 000 and even more particularly from 1000 to 200 000.

A silicone corresponding to this formula is, for example, DC2-8566 Amino Fluid from Dow Corning.

c) the amino silicones corresponding to formula (H):

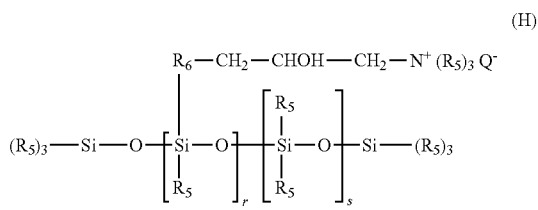
(H)

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;
- Q- is an anion such as a halide ion, especially chloride, or an organic acid salt, especially acetate;
- r represents a mean statistical value from 2 to 20 and in particular from 2 to 8;
- s represents a mean statistical value from 20 to 200 and in particular from 20 to 50.

Such amino silicones are especially described in patent U.S. Pat. No. 4,185,087;

d) the quaternary ammonium silicones of formula (I):

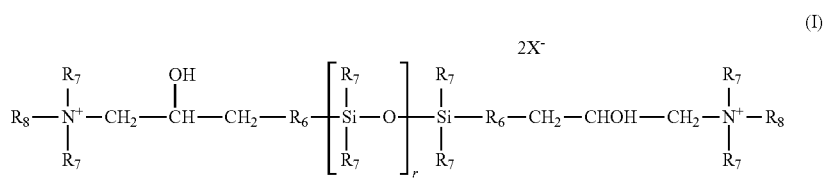
(I)

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—$NHCOR_7$;
- X— is an anion such as a halide ion, especially chloride, or an organic acid salt, especially acetate;
- r represents a mean statistical value ranging from 2 to 200 and in particular from 5 to 100.

These silicones are described, for example, in patent application EP-A 0 530 974.

e) the amino silicones of formula (J):

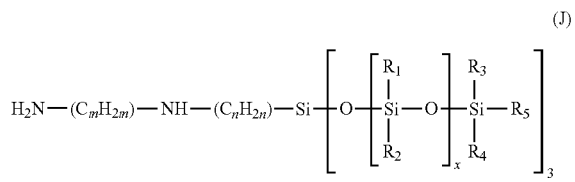

in which:
R$_1$, R$_2$, R$_3$ and R$_4$, which may be identical or different, denote a C$_1$-C$_4$ alkyl radical or a phenyl group,
R$_5$ denotes a C$_1$-C$_4$ alkyl radical or a hydroxyl group,
n is an integer ranging from 1 to 5,
m is an integer ranging from 1 to 5, and
x is chosen such that the amine number ranges from 0.01 to 1 meq/g;

f) the multiblock polyoxyalkylenated amino silicones, of the type (AB)n, A being a polysiloxane block and B being a polyoxyalkylene block comprising at least one amine group.

Said silicones preferably are constituted of repeating units of the following general formulae:

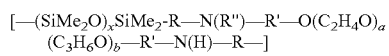

or alternatively

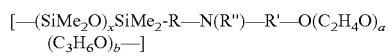

in which:
a is an integer greater than or equal to 1, preferably ranging from 5 to 200 and more particularly ranging from 10 to 100;
b is an integer between 0 and 200, preferably ranging from 4 to 100 and more particularly between 5 and 30;
x is an integer ranging from 1 to 10 000 and more particularly from 10 to 5000;
R" is a hydrogen atom or a methyl;
R, which may be identical or different, represent a divalent linear or branched C2-C12 hydrocarbon-based radical, optionally including one or more heteroatoms such as oxygen; preferably, R denotes an ethylene radical, a linear or branched propylene radical, a linear or branched butylene radical, or a —CH2CH2CH2OCH(OH)CH2- radical; preferentially R denotes a —CH2CH2CH2OCH(OH)CH2- radical;
R', which may be identical or different, represent a linear or branched C2-C12 divalent hydrocarbon-based radical, optionally comprising one or more heteroatoms such as oxygen; preferably, R' denotes an ethylene radical, a linear or branched propylene radical, a linear or branched butylene radical, or a —CH2CH2CH2OCH(OH)CH2- radical; preferentially, R' denotes —CH(CH3)-CH2-.

The siloxane blocks preferably represent between 50 mol % and 95 mol % of the total weight of the silicone, more particularly from 70 mol % to 85 mol %.

The amine content is preferably between 0.02 and 0.5 meq./g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may especially be made of the silicones sold under the name Silsoft A-843 or Silsoft A+ by Momentive.

g) and mixtures thereof.

Preferably, the amino silicones are chosen from multi-block polyoxyalkylenated amino silicones.

The functionalized silicone may be an alkoxy silicone, such as the product sold under the name Silicone Copolymer F-755 by SWS Silicones, and Abil Wax® 2428, 2434 and 2440 by the company Goldschmidt.

The functionalized silicone may be a silicone bearing hydroxyl group(s), for instance alpha,omega-dihydroxy terminated polydimethylsiloxanes, such as the compounds having the INCI name dimethiconol, alone or in emulsion or as a mixture, including the dimethicone/dimethiconol mixture sold under the name Xiameter PMX-1503 Fluid by Dow Corning or the dimethiconol/dimethicone/isohexadecane and isoparaffin mixture sold under the name Xiameter PMX-1503 Fluid by Dow Corning.

The composition that is useful in the process according to the invention may comprise the functionalized silicone(s), preferably amino silicones, in an amount ranging from 0.01% to 15% by weight, preferably from 0.05% to 10% by weight and preferentially from 0.1% to 5% by weight, relative to the total weight of the composition.

Fatty Substances

The composition may comprise one or more fatty substances other than the functionalized silicones as described previously.

The term "fatty substance" means an organic compound that is insoluble in water at ordinary temperature (25° C.) and at atmospheric pressure (760 mmHg; i.e. 1.013×10$^5$ Pa) (solubility of less than 5% and preferably of less than 1%, more preferably still of less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified carboxylic acid groups.

In addition, the fatty substances of the invention are not (poly)oxyalkylenated or (poly)glycerolated ethers.

The term "oil" means a "fatty substance" that is liquid at room temperature (25° C.) and at atmospheric pressure (760 mmHg or 1.013×10$^5$ Pa).

The term "non-silicone oil" means an oil not containing any silicon atoms (Si) and the term "silicone oil" means an oil containing at least one silicon atom.

More particularly, the fatty substance(s) are chosen from C6-C16 hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides and non-silicone waxes, in particular plant waxes, non-silicone waxes, and silicones other than the functionalized silicones, and mixtures thereof.

It is recalled that the fatty alcohols, esters and acids more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the C6-C16 hydrocarbons, they are more particularly linear or branched, and possibly cyclic, and are preferably alkanes. Examples that may be mentioned include hexane, cyclohexane, undecane, dodecane, tridecane or isoparaffins, such as isohexadecane, isodecane or isododecane, and mixtures thereof.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®, and mixtures thereof.

A hydrocarbon-based oil of animal origin that may be mentioned is perhydrosqualene.

The triglycerides of plant or synthetic origin are preferably chosen from liquid fatty acid triglycerides containing from 6 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 6 to 30 carbon atoms and preferably from 8 to 30 carbon atoms. Examples that may be mentioned include cetyl alcohol, isostearyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

As regards the esters of fatty acids and/or of fatty alcohols advantageously other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ and $C_1$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar and fatty acid esters may be chosen in particular from the group comprising the esters or mixtures of sugar esters described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleate or dioleate, stearate, behenate, oleopalmitate, linoleate, linolenate or oleostearate.

An example that may be mentioned is the product sold under the name Glucate® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose mono-dipalmito-stearate sold by the company Goldschmidt under the name Tegosoft® PSE.

The non-silicone wax(es) are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy raw materials that may be used according to the invention are in particular marine waxes, such as that sold by Sophim under the reference M82, polyethylene waxes or polyolefin waxes in general.

The silicones that may be used in the cosmetic composition of the present invention are volatile or non-volatile, cyclic, linear or branched silicones, which are unmodified or modified with organic groups, having a viscosity from $5\times10^{-6}$ to 2.5 $m^2/s$ at 25° C., and preferably $1\times10^{-5}$ to 1 $m^2/s$.

The silicones that may be used in accordance with the invention may be in the form of oils, waxes, resins or gums.

Preferably, the silicone(s) are chosen from polydialkylsiloxanes, especially polydimethylsiloxanes (PDMS).

Use is preferably made of non-volatile polydialkylsiloxanes, polydialkylsiloxane gums and resins, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200, with a viscosity of 60 000 mm2/s;

the Viscasil® oils from General Electric and certain oils of the SF series (SF 96, SF 18) from General Electric.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:

mixtures of a polydimethylsiloxane gum and of a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, and more particularly of a PDMS gum and of a PDMS oil, such as the product SF 1236 from the company General Electric. The product SF 1236 is a mixture of a gum SE 30 defined above with a viscosity of 20 $m^2/s$ and of an oil SF 96 with a viscosity of $5\times10^{-6}$ $m^2/s$. This product preferably comprises 15% of gum SE 30 and 85% of an oil SF 96.

The organopolysiloxane resins that may be used in accordance with the invention are crosslinked siloxane systems containing the following units:

R2SiO2/2, R3SiO1/2, RSiO3/2 and SiO4/2 in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate-type resins sold in particular under the names X22-4914, X21-5034 and X21-5037 by the company Shin-Etsu.

The polyalkylarylsiloxanes are chosen particularly from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, the fatty substance(s) are non-silicone.

The fatty substance(s) are advantageously chosen from hydrocarbons containing more than 16 carbon atoms, C6-C16 alkanes, triglycerides or oils of plant origin, liquid synthetic triglycerides, fatty alcohols, esters of fatty acids and/or of fatty alcohols other than triglycerides and non-silicone waxes, or mixtures thereof. More preferentially, the fatty substance(s) are chosen from liquid petroleum jelly and liquid fatty alcohols such as 2-octyldodecanol and stearyl alcohol.

Additives

The composition that is useful in the process according to the invention may also comprise one or more additives.

As additives that may be used in accordance with the invention, mention may be made of cationic polymers other than those mentioned above, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, opacifiers or nacreous agents, antioxidants, oxy acids, fragrances, preserving agents and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

Preferably, in the composition according to the invention, the pH ranges from 3 to 11 and preferably from 4 to 9.

The composition that is useful in the process according to the invention may be in the form of a wax, a paste, a cream, a foam, a spray (pump and aerosol) or a lotion. It may comprise one or more phases.

The composition may be applied to wet or dry hair, preferably wet hair, with or without a leave-on time.

In the case where a leave-on time is applied, it is between 2 minutes and 1 hour. The leave-on time may be applied with heat, and in particular under an exclusive system such as wrappers.

The bath ratio of the formulation applied to the hair may be between 0.05 and 10, and more particularly between 0.05 and 5.

The hair is optionally rinsed and/or manually dried before removing an excess of composition.

Heating Step

The step of placing the keratin fibres in contact with a heating means may be performed using any heating device.

One or more heating tools may be applied individually or successively to the hair.

The application of heat may be performed at a temperature of between 40 and 250° C., preferentially between 90° C. and 250° C. and more preferentially between 100° C. and 210° C.

The application of heat may be performed for a time of between 2 seconds and 1 hour and preferentially between 2 seconds and 1 minute.

The application of the heating means may take place by successive touches or by sliding the appliance along the fibres.

The heating tool may be a straightening iron, a curling iron, a crimping iron, a waving iron, a hood, a hairdryer, an infrared heating system or heating curlers.

The heat application step may take place before, during or after the step of applying the composition, preferably during or after the step of applying the composition. More preferentially, the heat application step takes place after the application of the composition. An optional leave-on time may intervene between the application of the composition and the application of heat.

Multi-Application

The steps of applying the composition and applying of heat as defined above may be implemented at least twice, preferably at least three times, more preferably at least five times.

According to one preferred embodiment, the invention deals with a process for treating keratin fibres, especially the hair, comprising the following steps:
  application to the keratin fibres of a composition comprising one or more cationic acrylic copolymers comprising at least the units obtained from the following monomers:
    a) monomer derived from acrylic or methacrylic esters or amides and comprising at least one cationic group, and
    b) alkyl acrylate or methacrylate monomer, and
  application of heat to the keratin fibres using a heating tool, the application of heat possibly taking place before, during or after the application of the composition, preferably during or after,
these successive steps being implemented at least twice, more preferably at least five times.

Indeed, the repeated process of applying to the keratin fibres of the composition according to the invention and then applying of heat to the keratin fibres gives the treated fibre an ever better coating of the fibre. In particular, said repeated process brings a very good effect in terms of frizz control.

EXAMPLES

I. Example 1

1. Preparation of the Compositions

Compositions A and B according to the invention and comparative composition C were prepared using the ingredients whose contents are indicated in the table below as weight percentages.

|  | A (inv) | B (inv) | C (comp) |
|---|---|---|---|
| Copolymer 1 (containing 30% active material in ethanol) (1) | 16.7 | 16.7 | — |
| Behenyltrimethylammonium chloride (79% AM, 18% isopropanol) (2) | — | 1 | — |
| Stearyl alcohol | — | 1.5 | — |
| PPG-5-Ceteth-20 | — | 0.2 | — |
| Phenoxyethanol | — | 0.7 | — |
| Ethanol | qs 100% | — | qs 100% |
| Water | — | qs 100% | — |

(1) Plascize L-514
(2) Genamine KPMD from Clariant

2. Application Protocol

The application protocols were as follows:

| Protocol according to the invention | Comparative protocol |
|---|---|
| Shampooing | Shampooing |
| Application of the composition onto wet natural straight hair | Application of the composition onto wet natural straight hair |
| Predrying with a hairdryer | Natural drying |
| Blow-drying with a hairdryer | |

3. Evaluation and Results

The evaluation protocol after drying is:
Evaluation of the impact on the shape, the cosmetic criteria (feel) and the appearance (macroscopic, TEM visualization)

The persistence evaluation protocol is as follows: Performing several cycles:
  Wetting of the hair
  Shampooing Rinsing Drying with a hairdryer Evaluation of the impact on the shape, the cosmetic criteria (feel) and the appearance (macroscopic, TEM visualization)

3.1 Macroscopic Aspects

Observations by scanning electron microscope (SEM) demonstrate the surface state of treated hair, on the day of application and after shampoo washes, and reveal the deposit of cosmetic product and its persistence.

With composition A according to the invention and by following the protocol according to the invention, homogeneous, uniform and covering coating of the fibre was observed. This coating is persistent for up to 10 shampoo washes.

With composition A according to the invention and by following the comparative protocol, non-homogeneous, non-uniform coating in the form of aggregates was observed. Furthermore, the deposit is only very sparingly persistent on the fibre after one shampoo wash and has completely disappeared after 10 shampoo washes.

Thus, heat allows better distribution and better adhesion of the polymer to the fibre, which allows persistence of the effects with respect to shampooing.

With comparative composition C and by following the protocol according to the invention, no coating is formed.

3.2 Cosmetic Aspects

With composition A according to the invention and by following the protocol according to the invention, the coating gives the head of hair a mass, body and styling effect and also reinforcement at T0 and after shampooing. The shaping is facilitated. The split ends are rewelded together, for up to at least 10 shampoo washes.

With composition A according to the invention and by following the comparative protocol, the lock has a non-uniform coated feel. There is no perceptible shaping or care effect after one shampoo wash/blow-drying cycle.

With comparative composition C and by following the protocol according to the invention, the feel was not modified.

II. Example 2

1. Preparation of the Compositions

Composition D according to the invention and comparative composition E were prepared using the ingredients indicated in the table below. The amounts are indicated in weight percentage of active material.

|  | D (inv) | E (comp) |
|---|---|---|
| Copolymer 1 (% am) (1) | 2 | — |
| Poly(2-methacryloxyethyltrimethylammonium chloride) (% am) (2) | — | 2 |
| Ethanol/Water (50/50) (% by weight) | qs 100% | qs 100% |

(1) Plascize L-514
(2) Polyquaternium-37

2. Application Protocol

Compositions D and E are applied on wet natural locks of hair, which have been beforehand washed with a standard shampoo. 0.15 g of composition per gram of locks is applied. Hair has then been predried with a hairdryer, and blowdried with a hairdryer.

3. Evaluation and Results

Performances in terms of mass effect have been evaluated on dried hair by five experts, on a scale from 0 (very bad) to 5 (very good):

| Scale | Evaluation |
|---|---|
| 0 | Very bad |
| 0.5 | Very bad/Bad |
| 1 | Bad |
| 1.5 | Fairly bad/Bad |
| 2 | Fairly bad |
| 2.5 | Average |
| 3 | Fairly good |
| 3.5 | Good/Fairly good |
| 4 | Good |
| 4.5 | Very good/Good |
| 5 | Very good |

The mass effect evaluation is tactile: the expert grabs the hair in his hand and evaluates, from the root to the tip, the amount of hair felt in his fingers.

In order to evaluate the mass effect persistence after one shampoo, locks of hair are washed with a standard shampoo, rinsed and then blowdried with a hairdryer.

Results are indicated in the table below:

|  | D (invention) | E (comparative) |
|---|---|---|
| After applying |  |  |
| Expert 1 | 4 | 3 |
| Expert 2 | 3 | 1 |
| Expert 3 | 4 | 2 |
| Expert 4 | 3.5 | 2.5 |
| Expert 5 | 4 | 3 |
| Mean | 3.7 | 2.3 |
| Standard deviation | 0.4 | 0.8 |
| After 1 shampoo |  |  |
| Expert 1 | 4 | 2 |
| Expert 2 | 3 | 1 |
| Expert 3 | 3.5 | 2 |
| Expert 4 | 4 | 3 |
| Expert 5 | 4 | 2 |
| Mean | 3.7 | 2 |
| Standard deviation | 0.4 | 0.7 |

Locks of hair, which has been treated by composition D according to the invention, have a better mass effect than locks of hair which have been treated by composition E.

These results are significant in relation to the standard deviations.

As a consequence, the mass effect, and its persistence, have been improved in comparison with the prior art.

III. Example 3

1. Preparation of the Compositions

Compositions F and G according to the invention, and comparative compositions H and I were prepared using the ingredients indicated in the table below. The amounts are indicated in weight percentage of active material.

|  | F (inv) | G (inv) | H (comp) | I (comp) |
|---|---|---|---|---|
| Copolymer 1 (% am) (1) | 1 | 5 | — | — |
| PEG-40/PPG-8 Methylaminopropyl/ hydroxypropyl dimethicone copolymer at 30% in a glycerin/dipropylene glycol/water mixture (% am) (2) | 0.4 | 2 | 0.4 | 2 |
| Ethanol/Water (50/50) (% by weight) | qs 100% | qs 100% | qs 100% | qs 100% |

(1) Plascize L-514
(2) Silsoft A+ from Momentive

2. Application Protocol

The application protocol was as follows:
Application of the compositions onto wet natural hair
Predrying with a hairdryer
Applying of hair iron
Shampooing The protocol using compositions F and H has been implemented five times whereas the protocol using compositions G and I has been implemented once. Therefore, the same amounts of active material, i.e. copolymer 1 and component (2) for compositions F and G, and component (2) for compositions H and I, are present on hair.

3. Results

The results in terms of frizz control are observed. The result linked to protocol, implemented five times, using composition F is observed in FIG. 2A whereas the result linked to protocol, implemented once, using composition G is observed in FIG. 2B. The result linked to protocol, implemented five times, using composition H is observed in FIG. 1A whereas the result linked to protocol, implemented once, using composition I is observed in FIG. 1B.

Figure 1B:
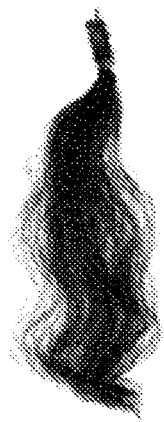
FIGS. 1B, and 2B are photographs of locks of hair on which different compositions have been applied once.
Figure 2A:
Figure 2B:
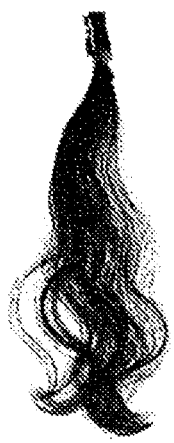

FIGS. 2A and 2B clearly show that a better result is observed than the one shown respectively by FIG. 1A and FIG. 1B. Indeed, the presence of the specific copolymer, comprised in the composition according to the invention, leads to a better individualization effect of the treated lock.

FIG. 2A clearly shows that a better result is observed than the one shown by Picture 2B. Indeed, the frizz control is also improved for hair shown on FIG. 2A. Thus, the repeated process of applying to the keratin fibres of the composition according to the invention and then applying of heat to the keratin fibres gives the treated fibre an ever better coating of the fibre than said process implemented once.

The invention claimed is:

1. A process for treating keratin fibres, the process comprising:
applying to the keratin fibres a composition comprising at least one cationic acrylic copolymer comprising at least the units obtained from the following monomers:
a) a monomer derived from acrylic or methacrylic esters or amides and comprising at least one cationic group, having the following formulae:

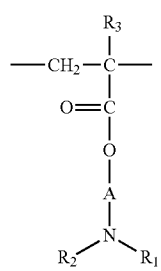

(I)

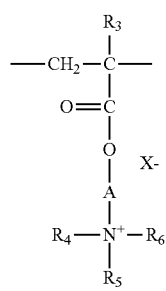

(II)

wherein:
$R_3$, which may be identical or different, denotes a hydrogen atom or a $CH_3$ group;
A, which may be identical or different, represents a linear or branched divalent alkyl group of 1 to 6 carbon atoms, or a hydroxyalkyl group of 1 to 4 carbon atoms;
$R_4$, $R_5$ and $R_6$, which may be identical or different, each represent an alkyl group containing from 1 to 18 carbon atoms or a benzyl group;
$R_1$ and $R_2$, which may be identical or different, each represent a hydrogen atom, or an alkyl group containing from 1 to 6 carbon atoms;
X represents an anion derived from a mineral or organic acid, a methosulfate anion, or a halide;
b) a $C_1$-$C_{30}$ alkyl acrylate or methacrylate monomer; and
c) a polymerizable ethylenic monomer having following formula:

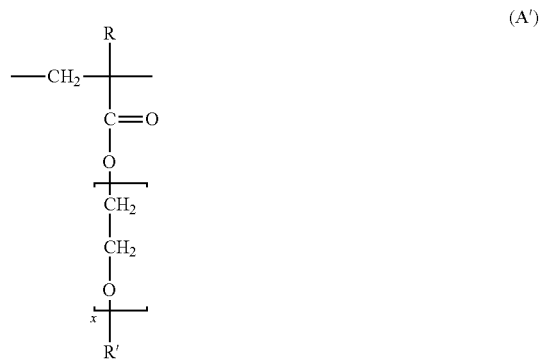

(A')

wherein:
R and R', which may be identical or different, each represents a hydrogen atom, or a $C_1$-$C_{10}$ alkyl radical; and
x ranges from 1 to 10; and
wherein the total amount of the at least one cationic acrylic copolymer ranges from 1% to 7% by weight, relative to the total weight of the composition; and
applying heat to keratin fibers using a heating tool, wherein applying heat occurs before, during, or after applying the composition.

2. The process according to claim 1, wherein the at least one cationic acrylic copolymer comprises at least the units obtained from the following monomers:
a) methacryloyloxyethyltrimethylammonium salt,
b) butyl methacrylate, and
c) ethoxy ethyl methacrylate.

3. The process according to claim 1, wherein the composition further comprises at least one additive chosen from a thickening polymer, a surfactant, a functionalized silicone, a fatty substance, or a mixture thereof.

4. The process according to claim 1, wherein heat is applied to the keratin fibres at between 40° C. and 250° C.

5. The process according to claim 1, wherein heat is applied to the keratin fibres for a time of between 2 seconds and 1 hour.

6. The process according to claim 1 wherein the heating tool is chosen from a straightening iron, a curling iron, a crimping iron, a waving iron, a hood, a hairdryer, an infrared heating system, heating curlers, or a combination thereof.

7. The process according to claim 1, wherein the bath ratio of the composition applied to the keratin fibres is between 0.05 and 10.

8. The process according to claim 1, wherein the applying heat occurs after applying the composition.

9. The process according to claim 1, wherein the applying the composition and the applying heat are implemented at least twice.

* * * * *